United States Patent [19]

Corby

[11] Patent Number: 5,635,492

[45] Date of Patent: Jun. 3, 1997

[54] TEAT TREATING COMPOSITIONS, PRODUCTION AND USE

[75] Inventor: Michael P. Corby, Ravenshead, England

[73] Assignee: Diversey Lever, Inc., Plymouth, Mich.

[21] Appl. No.: 754,505

[22] Filed: Sep. 3, 1991

[30] Foreign Application Priority Data

Aug. 31, 1990 [GB] United Kingdom ............... 9019984

[51] Int. Cl.$^6$ .................. A01N 43/04; A01N 25/00; C07G 17/00

[52] U.S. Cl. .................. 514/54; 514/782; 514/816; 536/114; 536/123; 424/670; 424/78.02

[58] Field of Search .................. 514/54, 730, 673, 514/568, 358, 782, 816; 536/114, 123; 424/78, 661, 672, 670, 81, 80, 78.02

[56] References Cited

U.S. PATENT DOCUMENTS

| | | | |
|---|---|---|---|
| 4,113,854 | 9/1978 | Andrews et al. | 424/78 |
| 4,140,766 | 2/1979 | Kalogris | 424/670 |
| 4,199,564 | 4/1980 | Silver et al. | 514/643 |
| 4,288,428 | 9/1981 | Föll et al. | 424/672 |
| 4,446,153 | 5/1984 | Yang et al. | 514/730 |
| 4,716,180 | 12/1987 | Fetty et al. | 514/782 |
| 4,891,216 | 1/1990 | Kross et al. | 424/661 |
| 4,945,110 | 7/1990 | Brokken et al. | 514/578 |
| 4,996,197 | 2/1991 | Mazuel | 536/114 |
| 5,063,249 | 11/1991 | Andrews | 514/564 |
| 5,079,348 | 1/1992 | Clare et al. | 536/114 |

FOREIGN PATENT DOCUMENTS

| | | |
|---|---|---|
| 0289160 | 11/1988 | European Pat. Off. . |
| 0300888 | 1/1989 | European Pat. Off. . |
| 2376662 | 8/1978 | France . |
| 8101516 | 6/1981 | WIPO . |

*Primary Examiner*—John Kight
*Assistant Examiner*—Louise Leary
*Attorney, Agent, or Firm*—A. Kate Huffman

[57] ABSTRACT

A teat-treating composition comprising a biocide in an aqueous medium characterised in that it also comprises a pseudo-plastically- or thixotropically-effective amount of Rhamsan gum is disclosed, as is the production thereof by mixing the components.

Such compositions may be used to counter mastitis, particularly in dairy cattle, by dipping or spraying cows' teats.

9 Claims, No Drawings

TEAT TREATING COMPOSITIONS, PRODUCTION AND USE

This invention relates to teat-treating compositions and to the production and use thereof; more particularly, it relates to "non-drip" teat dips and sprays.

The field of application of the present invention is not restricted to dairy cattle, but, this being the largest area of interest, it will be used for illustrative purposes at this time. For many years, in particular cows' teats have been sanitised immediately after milking in order to reduce the incidence of mastitis. This has generally been carried out by dipping or spraying the teats. Mastitis is a condition of microbiological colonisation of cows' milking organs. If contamination reaches a sufficiently high level due to either challenge or microbial growth, the clinical symptoms of mastitis become evident resulting, inter alia, in the additional expense to a farmer of milk loss, as well as veterinary treatment.

Known bovine teat dip or spray preparations include a variety of biocidal agents, such as iodine and chlorhexidine. Heretofore, it has always been the practice with non-barrier-forming teat dips to present the formulation in an essentially Newtonian state, i.e. a state with little or no shear-thinning. Some previous teat dips consisting essentially of a film-forming polymer latex have used non-Newtonian shear-thinning additives in order that a thick occlusive film forms on the teat. (See, for example, U.S. Pat. No. 4,113,854.) Other known formulations have incorporated polysaccharide thickening agents, such as the carboxy methyl celluloses. (See, for example, U.S. 4,376,787) Such thickeners provide a limited thixotropic effect in order to resist rapid draining or running off from the teat or udder. Until now, all such formulations have been thickened with a view to retaining material on the teat, but at the expense to the user of high usage rates. A large amount applied to the teat will result in more actually adhering despite run-off. The present invention makes possible for the first time the use of "normal" use rates, but with much higher retention percentages on the teats, thereby retaining more material on the teats without dramatic increases in use rate and without large percentages of an expensive material running off the teat onto the floor. Thus, greater efficiency is now available using current levels or, alternatively, levels may be reduced while retaining efficiency.

It has now surprisingly been found that the use of a microbial polysaccharide known as "Rhamsan gum" provides the desired thixotropic properties, while avoiding the need for film-forming polymers. (Rhamsan gum is the common name of a current product of Kelco International which may be characterised as D-glucopyranuronic acid polymer, with 6-deoxy-L-mannopyranose and D-glucopyranose, acetate, calcium potassium sodium salt. Having defined the intended material, the common name will be used for convenience.) It may be used as the sole thixotropic agent or in combination with one or more conventional thickeners. Surprisingly this material, when dispersed in an aqueous medium in combination with one or more microbiocides, typically iodine, aldehydes or alcohols, such as benzyl alcohol, chlorhexidine, or iodophors, produces non-drip formulations of biocidal character of particular value in dairy farming for the control of bovine mastitis. Such formulations will also typically contain one or more conventional excipient ingredients, such as preservatives, emollients, fly-repellents, alcohols, colourants, surfactants, buffers and sequestrants.

Accordingly, the present invention provides a teat-treating composition comprising a biocide in an aqueous medium characterised in that it also comprises a pseudo-plastically- or thixotropically-effective amount of Rhamsan gum.

For example, up to 2.0% w/w, more preferably up to 0.5% w/w of Rhamsan gum may be present. Such compositions may be formulated, optionally for further dilution, by mixing the ingredients and the present invention also provides such production. Furthermore, the present invention provides the use of such compositions to counter mastitis by the application of such compositions, in particular by dipping or spraying cows' teats.

The following is provided by way of further exemplification:

EXAMPLE 1

A typical iodine-based formulation comprised:

|  | % w/w |
|---|---|
| Iodophor complex (*) providing 0.5% w/w as titratable iodine | 2.8 |
| Isopropanol | 4.0 |
| Rhamsan gum | 0.3 |
| Surfactant (non-ionic; nonyl phenol 9 EO) | 3.0 |
| Glycerine | 10.0 |
| Water (soft) | Q.S. |

(*) { 72% nonyl phebol 12 EO
      28% iodine

The Rhamsan gum was dispersed in the isopropanol and the mixture was added to the water. It was stirred and heated to 50° C. to hydrate the gum, then cooled and to it added the surfactants, the glycerine and, finally, the iodophor complex sufficient to give a minimum of 0.5% w/w titratable iodine.

As mentioned above, the present compositions may be provided as concentrates for dilution by users. In the case of the following iodine-based formulation, which may be produced as illustrated above, one part product would normally be diluted with three parts of water.

EXAMPLE 2

|  | % w/w |
|---|---|
| Iodophor complex sufficient to give 2% w/w titratable iodine | 10.1 |
| Isopropanol | 4.0 |
| Rhamsan gum | 0.4 |
| Surfactants (non-ionic; nonyl phenol 9 EO) | 13.0 |
| Glycerine | 14.0 |
| Sorbitol (70%) | 14.0 |
| Water (soft) | Q.S. |

Surprisingly, the concentrate is not too viscous to handle easily, while the diluted product retains the desirable characteristics.

EXAMPLE 3

A teat dip in accordance with the present invention may comprise benzyl alcohol as the active ingredient:

| | % w/w |
|---|---|
| Benzyl alcohol | 4.0 |
| Rhamsan gum | 0.1 |
| Surfactant (anionic; dodecylbenzene sulphonic acid) | 2.0 |
| Buffer (phosphate pH 7.0) | 1.0 |
| Blue dye (food grade anionic) | 0.003 |
| Glycerine | 10.0 |
| Water (soft) | Q.S. |

A dispersion of the Rhamsan gum in the benzyl alcohol was mixed with the water. The mixture was heated (50° C.) to hydrate the gum, then cooled and the other ingredients added in any order.

Similar production techniques are applied when other active ingredients are used:

EXAMPLE 4

| | % w/w |
|---|---|
| Chlorhexidine gluconate BP (20%) | 2.25 |
| Surfactants (non-ionic; $C_{12}$–$C_{14}$ linear alcohol 7.5 EO 4.5 PO $C_8$–$C_{10}$ 10 EO 80%) | 1.00 |
| Glycerine | 5.00 |
| Rhamsan gum | 0.15 |
| Isopropanol | 5.0 |
| Citric acid | 1.5 |
| Caustic soda | to pH 6.5 |
| Water (soft) | Q.S. |

EXAMPLE 5

| | % w/w |
|---|---|
| Glutaraldehyde (50%) | 1.0 |
| Surfactant (non-ionic; $C_{12}$–$C_{14}$ linear alcohol 7.5 EP 4.5 PO) | 0.5 |
| Isopropanol | 5.0 |
| Glycerine | 5.0 |
| Rhamsan gum | 0.1 |
| Colour (food grade anionic dye) | 0.001 |
| Water (soft) | Q.S. |

EXAMPLE 6

The present invention may also be applied to the production of an emulsified composition:

| | % w/w |
|---|---|
| Chlorhexidine digluconate | 2.25 |
| Ethylan CPG 7545 ($C_{12}$–$C_{14}$ linear alcohol 7.5 EO 4.5 PO) | 0.5 |
| Empilan KA 1080 ($C_8$–$C_{10}$ 10 EP 80%) | 0.5 |
| Glycerine | 5.0 |
| Rhamsan Gum | 0.15 |
| Imsol A (Isopropanol/water 85%/15%) | 5.0 |
| Citric acid | 1.5 |
| Water | Q.S. |
| Dye (Edicol ponceau 4R E124) | 0.001 |
| Caustic soda | to pH 6.5 |
| WOM 14 premix | 2.72 |
| (WOM 14 premix: | |
| Whitemore WOM 14 (white oil medicine grade 14) | 73.5 |
| Ethylan TU (nonyl phenol 8 E.O.) | 7.0 |
| Ethylan D253 ($C_{13}$–$C_{15}$ 3 EO) | 19.5) |

The Rhamsan gum was suspended in the Imsol A. While stirring quickly, the water was added and the gum was hydrated at 50° C. for 30 minutes. The citric acid, dye, Ethylan CPG 7545, Empilan KA 1080 and glycerine were added with stirring. The pH was adjusted to 6.5 using NaOH. The chlorhexidine digluconate was added with stirring. Using a high speed stirrer, the WOM 14 premix was added to the centre of the vortex and mixing was continued for 5 minutes.

The surprisingly advantageous effect of utilising Rhamsan gum in these formulations may be assessed very simply in the laboratory. Excised cows' teats were dipped in the products under examination and the weight used is measured, after each teat is dipped, as the weight loss from the cup used and the weight retained on the teat is measured by weighing the material run off and subtracting it from the weight used. Ten teats are used in each case and results are expressed as percentage retention efficiency. The entire exercise was duplicated and the retention efficiency is quoted as the mean of two replicates (i.e. 20 determinations on 10 tests).

Comparison results of a typical teat dip of the current generation would be for "Deosan Teatcare", a chlorhexidine-based non-thickened water-thin material that has been marketed for over twelve years:

| | |
|---|---|
| Amount used | 0.21 g/teat |
| Amount retained | 0.079 g/teat |
| Retention efficiency | 38%. |

Another example is of a thickened formulation available from Economics Laboratories as "Blugard":

| | |
|---|---|
| Amount used | 0.58 g/teat |
| Amount retained | 0.119 g/teat |
| Retention efficiency | 20%. |

A further comparison would be a typical iodophor product available from Ciba Geigy Ltd as "Superdip":

| | |
|---|---|
| Amount used | 0.33 g/teat |
| Amount retained | 0.13 g/teat |
| Retention efficiency | 39%. |

However, in accordance with the present invention:

| Example 1 | |
|---|---|
| Amount used | 0.64 g/teat |
| Amount retained | 0.634 g/teat |
| Retention efficiency | 99% |
| Example 2 | |
| Amount used | 0.34 g/teat |
| Amount retained | 0.22 g/teat |
| Retention efficiency | 65% |

| | Example 3 | |
|---|---|---|
| | Amount used | 0.19 g/teat |
| | Amount retained | 0.167 g/teat |
| | Retention efficiency | 88% |
| | Example 4 | |
| | Amount used | 0.35 g/teat |
| | Amount retained | 0.27 g/teat |
| | Retention efficiency | 77% |
| | Example 5 | |
| | Amount used | 0.45 g/teat |
| | Amount retained | 0.30 g/teat |
| | Retention efficiency | 67% |
| | Example 6 | |
| | Amount used | 0.347 g/teat |
| | Amount retained | 0.284 g/teat |
| | Retention efficiency | 82% |

Thus, it may be seen that the present invention provides significantly higher retention efficiency than current products, thickened or not thickened.

Moreover, the surprising advantages of the use of Rhamsan gum in accordance with the present invention are further demonstrated by the following comparisons, which include some common thickeners.

| (A-1) | Water | 100% |
|---|---|---|
| | Amount used | 0.120 g/teat |
| | Amount retained | 0.056 g/teat |
| | Retention efficiency | 47% |
| (A-2) | Water | 99.9% |
| | Carboxymethyl cellulose | 0.1% w/w |
| | Amount used | 0.13 g/teat |
| | Amount retained | 0.07 g/teat |
| | Retention efficiency | 54% |
| (A-3) | Water | 99.9% |
| | Xanthan gum | 0.1% w/w |
| | Amount used | 0.14 g/teat |
| | Amount retained | 0.08 g/teat |
| | Retention efficiency | 57% |
| (A-4) | Water | 99.9% |
| | Rhamsan gum | 0.1% |
| | Amount used | 0.10 g/teat |
| | Amount retained | 0.08 g/teat |
| | Retention efficiency | 80% |
| (B-1) | | % w/w |
| | Iodophor complex providing 0.5% w/w as titratable iodine | 2.8 |
| | Isopropanol | 4.0 |
| | Xanthan gum | 0.1 |
| | Surfactants (non-ionic) | 3.0 |
| | Glycerine | 10.0 |
| | Water | Q.S. |
| Results of test: | | |
| | Amount used | 0.58 g/teat |
| | Amount retained | 0.27 g/teat |
| | Retention efficiency | 46% |
| (B-2) | As (B-1) except: | |
| | Rhamsan gum | 0.1% w/w (in place of Xanthan gum) |
| Results of test: | | |
| | Amount used | 0.57 g/teat |
| | Amount retained | 0.40 g/teat |
| | Retention efficiency | 70% |
| (C-1) | | % w/w |
| | Benzyl alcohol | 4.0 |
| | Surfactant (anionic) | 2.0 |
| | Glycerine | 5.0 |
| | Phosphoric acid | 0.2 |
| | Caustic soda | to pH 7 |
| | Colour (food grade anionic) | 0.002 |
| | Water | Q.S. |
| Results of test: | | |
| | Amount used | 0.090 g/teat |
| | Amount retained | 0.047 g/teat |
| | Retention efficiency | 52% |
| (C-2) | As for (C-1), but plus 0.1% w/w Xantham gum. | |
| Results of test: | | |
| | Amount used | 0.29 g/teat |
| | Amount retained | 0.17 g/teat |
| | Retention efficiency | 59% |
| (C-3) | As for (C-1), but plus 0.2% w/w Xantham gum. | |
| Results of test: | | |
| | Amount used | 0.18 g/teat |
| | Amount retained | 0.10 g/teat |
| | Retention efficiency | 56% |
| (C-4) | As for (C-1), but plus 0.1% w/w Rhamsan gum. | |
| Result of text: | | |
| | Amount used | 0.110 g/teat |
| | Amount retained | 0.097 g/teat |
| | Retention efficiency | 88% |
| (C-5) | As for (C-1), but plus 0.2% w/w Rhamsan gum. | |
| Results of test: | | |
| | Amount used | 0.082 g/teat |
| | Amount retained | 0.077 g/teat |
| | Retention efficiency | 94% |

Compared to (C-1), it will be readily appreciated that (C-2) and (C-3) show no significant effect on retention efficiency due to the Xanthan gum, while (C-4) and (C-5) illustrate the highly significant improvement provided by the Rhamsan gum.

I claim:

1. An antimicrobial teat-treating composition, comprising:
   a biocide present in an amount effective to treat or prevent bovine mastitis;
   a pseudo-plastically or thixtropically-effective amount of Rhamsan gum:
   an aqueous medium, and
   wherein the composition, when applied to a teats provides at least 65% retention efficiency, the retention efficiency being the percentage of the composition retained on the teat compared to the amount of composition applied thereonto.

2. A composition as claimed in claim 1 wherein the amount of Rhamsan gum is up to 2.0% w/w.

3. A composition as claimed in claim 2 wherein the amount of Rhamsan gum is up to 0.5% w/w.

4. A composition as claimed in claim 1 wherein the biocide is selected from the group consisting of benzyl alcohol chlorhexide, iodine, iodophors and mixtures thereof.

5. A composition as claimed in claim 1 additionally comprising: an excipient.

6. A process for the production of a composition as claimed in claim 1 which comprises:
   hydrating the gum, and mixing together the components of said composition.

7. A method for treating or preventing bovine mastitis which comprises:
   applying, to the teats of a cow, the composition of claim 1.

8. The composition of claim 1 wherein the composition is a concentrate.

9. A teat dip use solution comprising:
   (a) one part of the concentrate of claim 8; and
   (b) about 3 parts of water.

* * * * *